(12) United States Patent
Schirra et al.

(10) Patent No.: US 9,750,471 B2
(45) Date of Patent: Sep. 5, 2017

(54) PHOTON-COUNTING DETECTOR CALIBRATION

(71) Applicant: KONINKLIJKE PHILIPS N.V., Eindhoven (NL)

(72) Inventors: Carsten Oliver Schirra, St. Louis, MO (US); Axel Thran, Hamburg (DE); Heiner Daerr, Hamburg (DE); Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/889,899

(22) PCT Filed: May 10, 2014

(86) PCT No.: PCT/IB2014/061357
§ 371 (c)(1),
(2) Date: Nov. 9, 2015

(87) PCT Pub. No.: WO2014/181315
PCT Pub. Date: Nov. 13, 2014

(65) Prior Publication Data
US 2016/0113603 A1    Apr. 28, 2016

Related U.S. Application Data

(60) Provisional application No. 61/821,773, filed on May 10, 2013.

(51) Int. Cl.
*G06F 19/00* (2011.01)
*G01N 21/00* (2006.01)
(Continued)

(52) U.S. Cl.
CPC ............ *A61B 6/4241* (2013.01); *A61B 6/032* (2013.01); *A61B 6/482* (2013.01); *A61B 6/583* (2013.01);
(Continued)

(58) Field of Classification Search
CPC ........ G06F 19/00; G01N 21/00; G01D 18/00; A61B 6/032; A61B 6/4241; G01T 1/005; G01T 1/161; G01T 1/169
See application file for complete search history.

(56) References Cited

U.S. PATENT DOCUMENTS 6,362,471 B1    3/2002 Spitz et al.
6,683,934 B1    1/2004 Zhao et al.
(Continued)

FOREIGN PATENT DOCUMENTS

WO    2007092696 A2    8/2007

OTHER PUBLICATIONS

Alvarez, R. E.; Estimator for photon counting energy selective x-ray imaging with multibin pulse height analysis; 2011; Med. Phys.; 38(5)2324-2334.

(Continued)

*Primary Examiner* — David Porta
*Assistant Examiner* — Faye Boosalis (57) ABSTRACT

A method includes determining calibration factors for calibrating photon-counting detectors of a spectral imaging system by combining a heuristic calibration of the photon-counting detectors and an analytical calibration of the photon-counting detectors and generating a set of photon-counting calibration factors based on the combining of the a heuristic calibration and the analytical calibration. The photon-counting calibration factors, when applied to measured energy-resolved data from the photon-counting detectors of a spectral CT scan of a subject or object, mitigate spectral distortion caused by a radiation intensity profile shaper that filters a radiation beam of the spectral CT scan.

21 Claims, 4 Drawing Sheets

(51) Int. Cl.
G01D 18/00 (2006.01)
A61B 6/00 (2006.01)
A61B 6/03 (2006.01)
G01T 1/169 (2006.01)
G01T 7/00 (2006.01)
G01T 1/161 (2006.01)

(52) U.S. Cl.
CPC .............. *A61B 6/585* (2013.01); *G01T 1/161* (2013.01); *G01T 1/169* (2013.01); *G01T 7/005* (2013.01); *A61B 6/4233* (2013.01)

(56) References Cited

U.S. PATENT DOCUMENTS

2007/0140416 A1 6/2007 Nukui
2013/0077844 A1 3/2013 Vija et al.

OTHER PUBLICATIONS

Chuang, K-S., et al.; Comparison of four dual energy image decomposition methods; 1988; Phys. Med. Biol.; 33(4) 455-466.

Schlomka, J. P. et al.; Experimental feasibility of multi-energy photon-counting K-edge imaging in pre-clinical computed tomography; 2008; Phys. Med. Biol.; 53:4031-4047.

Stenner, P., et al.; Empirical dual energy calibration (EDEC) for cone-beam computed tomography; 2007; Med. Phys.; 34(9)3630-3641.

FIG. 5 ated as WO 2014/181315 A1 on Nov. 13, 2014, which
PHOTON-COUNTING DETECTOR CALIBRATION

CROSS REFERENCE TO RELATED APPLICATIONS

This application is a national filing of PCT application Serial No. PCT/IB2014/061357, filed May 10, 2014, published as WO 2014/181315 A1 on Nov. 13, 2014, which claims the benefit of U.S. provisional application Ser. No. 61/821,773 filed May 10, 2013, which is incorporated herein by reference.

The following generally relates to calibrating imaging detectors and more particularly to calibrating photon-counting imaging detectors, and is described with particular application to spectral computed tomography (CT).

A non-spectral CT scanner includes an x-ray tube mounted on a rotatable gantry opposite a detector array located across an examination region. The rotatable gantry, and hence the x-ray tube, rotates around the examination region. The x-ray tube is configured to emit x-ray radiation. A radiation intensity profile shaper such as the well-known "bow-tie" filter attenuates the emitted x-ray radiation directed towards the examination region to a greater degree at peripheral regions, relative to a more central region, thereby reducing the flux at the outer regions, which improves radiation efficiency.

A source collimator collimates the filtered x-ray radiation, producing a radiation beam in the direction of the examination region. The filtered radiation beam traverses the examination region (and a subject or object therein), and is detected by a detector array, which includes a one or two dimensional array of detector pixels. The detector pixels, in response, generate and outputs signals indicative of the detected radiation. The signal can be reconstructed to generate volumetric image data. Additionally, the volumetric image data can be processed to generate one or more images of the subject or object.

A spectral CT scanner has included the above-discussed elements with the addition of photon-counting detector pixels (e.g., CdTe, CdZnTe, etc.) (and, optionally multiple sources, kVp switching, etc.). Unfortunately, the bow-tie filter alters the primary beam spectrum of the x-ray source. That is, while the spectrum in front of the bow-tie filter can be considered homogenous for all angles, spectral distortions are caused by the bow-tie filter material, and the shape of the bow-tie filter results in variations in fan angle direction. Due to the spectral distortions, the calibration scheme for non-photon-counting detectors is not well-suited for photon counting detectors Photon counting detector calibration approaches generally fall under two approaches: heuristic and analytical (mathematical). Heuristic calibration approaches, from the literature, map a known set of absorber compositions to detector signals, which is subsequently used as a look-up table for material decomposition. However, this technique requires a calibration phantom whose complexity increases with the number of detector pixels and number of absorber materials, since each material combination that may occur in measured objects, has to be realized in the calibration procedure or an equivalent pair of absorbers.

For example, in order to acquire calibration data for medical CT, a calibration procedure has to be performed, where all combinations of all relevant thicknesses of bone, e.g., 0-10 cm, and all relevant thicknesses of soft tissue, e.g., 0-40 cm, have to be taken into account. A suitable procedure would be to produce two step phantoms of materials with similar x-ray attenuation properties as bone and soft tissue, e.g., aluminum and a polymer, respectively, and acquire data for all combinations of step numbers of both step phantoms.

In order to allow varying properties of individual pixels or the angle dependence of the x-ray spectrum, the calibration data would have to be acquired for all detector pixels. For example, a step phantom comprising 10 material thicknesses each, a total of 100 individual measurements would have to be made for each pixel. With a third material, e.g., iodine or another contrast agent, a third material would have to be included, adding an additional dimension to the calibration procedure.

In contrast, analytical approaches, from the literature, describe the polychromatic attenuation and detector physics. While these methods allow calculating the detector readout explicitly, precise knowledge of x-ray source spectrum, attenuation cross-sections and detector properties are required. In particular, the pixel-dependent variation of detector gain, detector sensitivity and pulse pile-up effects impose a significant challenge to this type of methods. As such, analytical approaches have been complex and not accurate.

In view of the above, there is an unresolved need for other approaches for calibrating photon-counting detectors.

Aspects described herein address the above-referenced problems and others.

The following describes a photon-counting detector calibration. Generally, a beam intensity profile shaper such as the well-known "bow-tie" filter causes spectral distortions in the x-ray beam. The approach described herein compensates for such spectral distortions, along with mitigating variations in detector gain, pulse pile-up effects, and/or other imperfections in the measurement chain that may impact decomposition and/or reconstruction quality.

In one aspect, a method includes determining calibration factors for calibrating photon-counting detectors of a spectral imaging system by combining a heuristic calibration of the photon-counting detectors and an analytical calibration of the photon-counting detectors and generating a set of photon-counting calibration factors based on the combining of the a heuristic calibration and the analytical calibration. The photon-counting calibration factors, when applied to measured energy-resolved data from the photon-counting detectors of a spectral CT scan of a subject or object, mitigate spectral distortion caused by a radiation intensity profile shaper that filters a radiation beam of the spectral CT scan.

In another aspect, a method including calibrating photon-counting detector pixels of a spectral imaging system by applying a set of calibration factors to each measured value of each detector pixel/energy bin pair, wherein the calibration factors are determined based on a combination of a heuristic calibration of the photon-counting detector and an analytical calibration of the photon-counting detector. The calibration factors mitigate spectral distortion caused by a radiation intensity profile shaper that filters a radiation beam of a spectral CT scan performed by the spectral imaging system.

In another aspect, a system includes a calibration factor generator that determines a set of photon-counting calibration factors for photon-counting detector pixels of a spectral CT imaging system. The calibration factor generator determines the set of photon-counting calibration factors based on counts for each detector pixel, energy bin, and thicknesses combination from data from a single scan, by the spectral CT imaging system, of a plurality of steps of a single phantom composed of a single material, where each step has a known and different approximately uniform thickness, and an analytical model that estimates counts for the same detector pixel, energy bin, and thicknesses combinations. The system further includes a data corrector that corrects measured data from the photon-counting detector pixels of subject or object produced in response to a scan of the subject or object with the spectral CT imaging system based on the set of photon-counting calibration factors.

The invention may take form in various components and arrangements of components, and in various steps and arrangements of steps. The drawings are only for purposes of illustrating the preferred embodiments and are not to be construed as limiting the invention.

The following describes a photon-counting detector calibration. The calibration includes performing a single scan of a single phantom composed of a single material and a plurality of different but uniform thickness steps, and mapping the results to an analytical (mathematical) model to generate calibration (or scaling) factors, which can then be subsequently applied to measured signals from a scan of subject or object to calibrate or convert the measured signals to match the analytical model, thereby correcting the measured data and generating corrected measured data.

Figure 1:
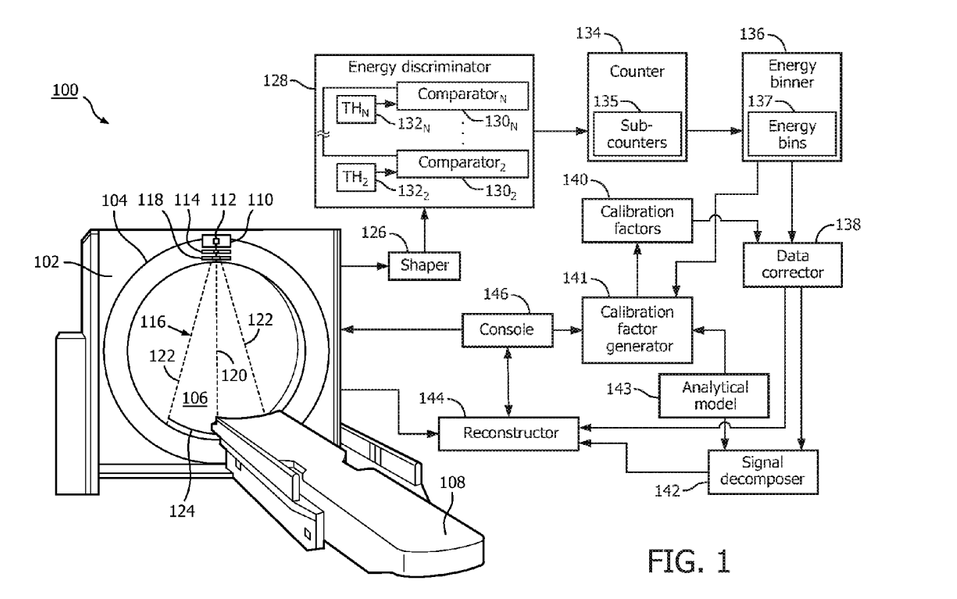
FIG. 1 schematically illustrates an example imaging system in connection with a data corrector that corrects measured signals for spectral distortions in the x-ray beam via calibration factors.

Initially referring to FIG. 1, an imaging system 100 such as a computed tomography (CT) scanner is schematically illustrated.

The imaging system 100 includes a stationary gantry 102 and a rotating gantry 104, which is rotatably supported by the stationary gantry 102. The rotating gantry 104 rotates around an examination region 106 about a longitudinal or z-axis. A subject support 108, such as a couch, supports an object or subject in the examination region 106. The subject support 108 can be used to vertically and/or horizontally position the subject or object relative to the imaging system 100 before, during, and/or after scanning.

A radiation source 110, such as an x-ray tube, is supported by and rotates with the rotating gantry 104 around the examination region 106 about the longitudinal or z-axis. The radiation source 110 includes a focal spot 112 that emits poly-energetic ionizing radiation at least in a direction of the examination region 106. A source collimator 114 collimates the radiation traversing in the direction of the examination region 106, producing a beam 116 having a pre-determined geometrical shape of interest, such as a fan, a cone, a wedge, or other shaped beam that traverses the examination region 106.

A radiation intensity profile shaper 118 is arranged between the focal spot 112 and the source collimator 114. In the illustrated embodiment, the radiation intensity profile shaper 114 includes a "bow-tie" filter, which, as discussed herein, shapes an intensity profile of radiation traversing there through such that transmission is greater nearer a central ray 120 of the beam 116 and decreases in a direction away from the ray 120 and towards outer rays 122 of the beam 116, and causes spectral distortions. Other beam intensity profile shapers are also contemplated herein.

A detector array 124 subtends an angular arc opposite the examination region 106 relative to the radiation source 110. The illustrated detector array 124 includes a one or two dimensional array of photon counting detector pixels such as direct conversion detector pixels, which include a direct conversion material such as cadmium telluride (CdTe), cadmium zinc telluride (CZT), and/or other direct conversion material. The detector array 124 detects radiation traversing the examination region 106 and generates a signal indicative of an energy thereof.

A pulse shaper 126 receives the signal generated by the detector array 124 and generates a pulse (e.g., a voltage or a current pulse) having a height or amplitude peak that is indicative of the energy of the corresponding incident detected radiation. Optionally, a pre-amplifier can be employed to amplify the signal prior to the pulse shaper 126 generating the pulse. Other pre-processing and/or conditioning can additionally or alternatively be applied to the signal before and/or after pulse shaping.

An energy discriminator 128 includes comparators $130_1$, ..., $130_N$ (referred to collectively herein as comparators 130) and respective energy thresholds (TH) $132_1$, ... $132_N$ (referred to collectively herein as thresholds 130), where N is an integer equal to or greater than one. The comparators 130 compare amplitudes (heights) of incoming pulses to the thresholds 132 and generate output signals that indicate which of the thresholds 132 were exceeded by the amplitudes of the pulses, thereby energy-discriminating the incoming pulses based on the thresholds 130.

A counter 134 increments a count value of a sub-counter 135 for each threshold based on the output of the energy discriminator 128. For instance, when the output of a comparator for a particular threshold indicates that an amplitude of a pulse exceeds the corresponding threshold, the count value for that threshold is incremented. An energy binner 136 energy bins the counts based on a plurality of bins, each bin representing a different energy range. For example, a photon resulting in a count for the lower threshold but not for a next higher threshold, would be assigned to the lower threshold bin.

A data processor 138 processes the binned measured signals. As described in greater detail below, such processing includes, but is not limited to, applying a set of predetermined calibration factors 140 to the binned measured signals. The calibration factors 140, in one instance, compensates for the spectral distortions caused by the material of the radiation intensity profile shaper 118. For example, this can be achieved by fitting the measured signals to an analytical model.

A calibration factor generator 141 generates the calibration factors 140. As described in greater detail below, the calibration factors 140 can be generated based on a hybrid approach, which includes a combination of a heuristic approach (i.e., the output of the energy binner 136) and an analytical approach (i.e., an analytical model 143 and scan protocol parameters from the console 146). Generally, the analytical approach models the attenuation by an absorber composed on any material combination and the detection physics, and the heuristic approach employs measured data that inherently includes hardware specific deviations from the analytical model.

The resulting calibration reduces the number of calibration steps (relative to a configuration which does not utilizes the hybrid calibration), while enabling the processing of an arbitrary number of different absorber materials, e.g. several contrast agents or even combinations thereof. The calibration factors may also compensate for pulse pile-up effects, variations in detector gain, and/or other imperfections in the measurement chain that may impact spectral decomposition quality and/or spectral reconstruction quality, even though these are not explicitly accounted for in the calibration.

At least one or more of the data corrector 138 or the calibration factor generator 141 is implemented via a hardware processor (e.g., a central processing unit, or CPU) executing one or more computer readable instructions encoded or embedded on computer readable storage medium (non-transitory medium), such as a physical memory device, and does not include transitory medium such a carrier wave, a signal, etc. Additionally or alternatively, at least one of the one or more computer readable instructions executed by the processor is carried by transitory medium.

At least one or more of the data corrector 138 or the calibration factor generator 141 can be part of the console 146 or external therefrom, for example, part of a separate computing system. In the later instance, the data corrector 138 and the calibration factor generator 141 can be part of a same separate computing system or different separate computing systems.

A signal decomposer 142 decomposes the corrected signals into various energy dependent components using the analytical model 143. In one instance, this may include decomposing the corrected signal into a Compton, a photo-electric, and/or (optionally) one or more K-edge components. A reconstructor 144 selectively reconstructs the detected and/or decomposed signals. In one instance, this includes reconstructing the Compton, photo-electric, and/or K-edge components, individually or in combination. From this, one or more anatomical (e.g., bone and soft tissue) and/or other material images (e.g., contrast agent) can be produced.

A computer serves as an operator console 146. The console 146 includes a human readable output device such as a monitor or display and an input device such as a keyboard and mouse. Software resident on the console 146 allows the operator to interact with the scanner 100 via a graphical user interface (GUI) or otherwise. This interaction may include initiating a scan, such as a photon-detector calibration scan of a calibration phantom or a scan of a subject or object, etc., invoking correction of the measured data of the scan with calibration factors from the calibration scan, etc.

Figure 2:
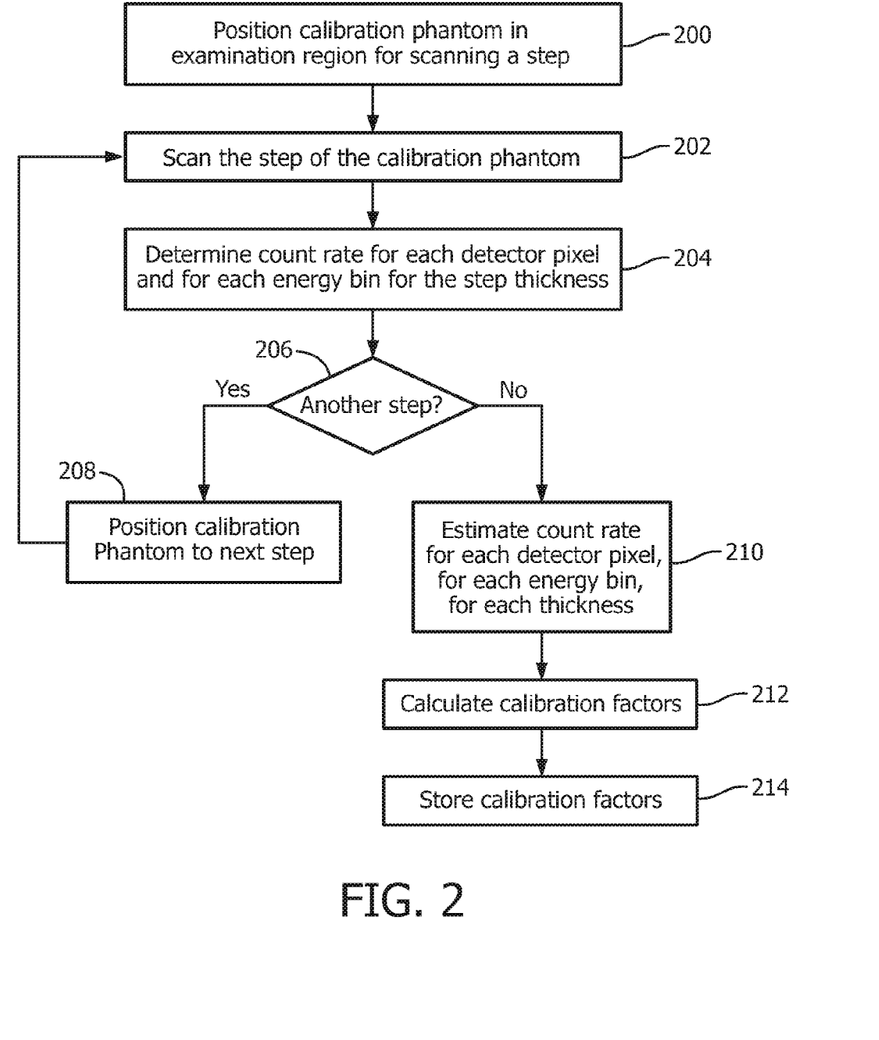
FIG. 2 illustrates an example method for determining the calibration factors.
Figure 3:
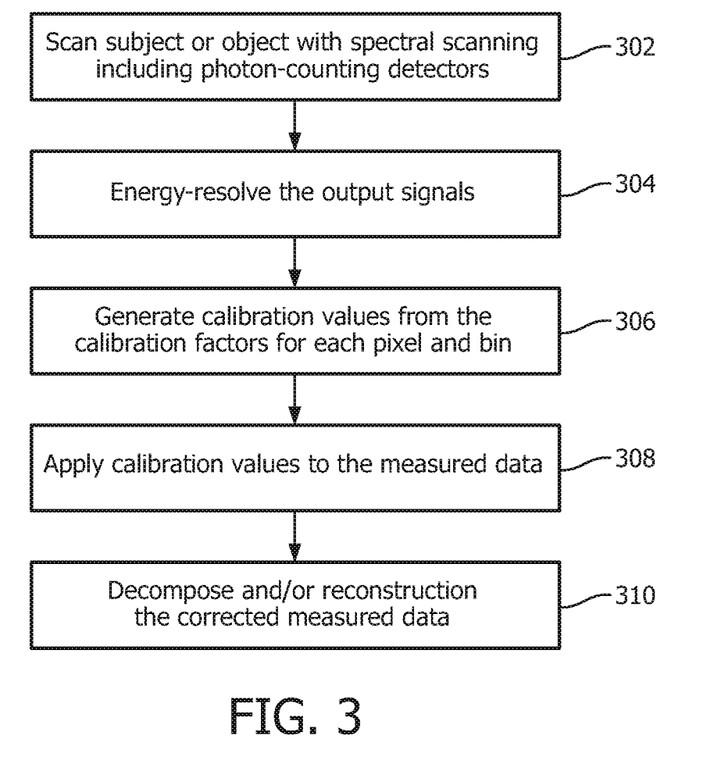
FIG. 3 illustrates an example method for employing the calibration factors.

FIGS. 2 and 3 respectively illustrate example methods for determining and using detector photon-counting detector calibration factors.

It is to be appreciated that the ordering of the acts of these methods is not limiting. As such, other orderings are contemplated herein. In addition, one or more acts may be omitted and/or one or more additional acts may be included.

Turning to FIG. 2, an example method for determining photon-counting detector calibration factors is illustrated.

This method includes scanning a calibration phantom. Briefly turning the FIG. 4, an example calibration phantom 402 is described. The illustrated calibration phantom is composed of a single material. Examples of suitable materials include, but are not limited to a thermoplastic such as polymethylmethacrylate (PMMA), a polycarboate, and/or other thermoplastic, aluminum, and/or other material.

Figure 4:
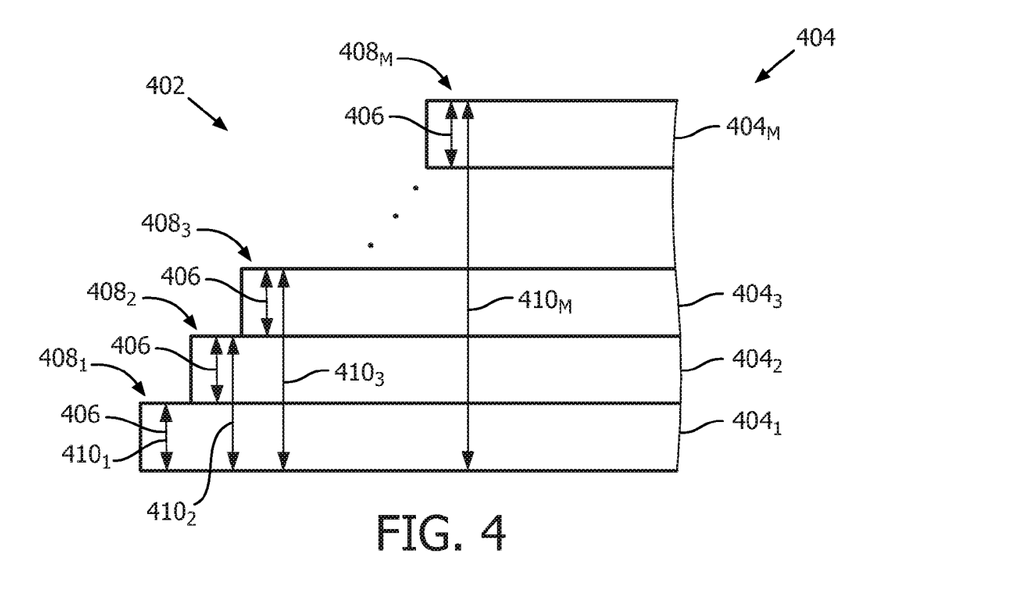
FIG. 4 schematically illustrates an example calibration phantom that includes a plurality of stacked and offset sheets of uniformly thick material affixed together.

Furthermore, the illustrated calibration phantom 402 includes M (where M is an integer greater than one) sheets 404 of the material, including a sheet $404_1$, a sheet $404_2$, sheet $404_3$, . . . , a sheet $404_M$. In this example, the sheets 404 have approximately the same thickness 406. In a variation, at least one sheet may have a different, but known, thickness. Furthermore, the thickness across each of the sheets 404 is approximately uniform.

In FIG. 4, the sheet $404_2$ is stacked on and affixed to the sheet $404_1$, physically offset therefrom along a longitudinal axis forming two regions $408_1$ and $408_2$ respectively having a first thickness $410_1$ (which is the thickness 406) and a second thickness $410_2$ (which is approximately 2×the thickness 406). Such stacking continues, forming regions $408_3$, . . . , and $408_M$ having a third thickness $410_3$ (which is approximately 3×the thickness 406), . . . , and an Mth thickness (which is approximately M×the thickness 406).

Figure 5:
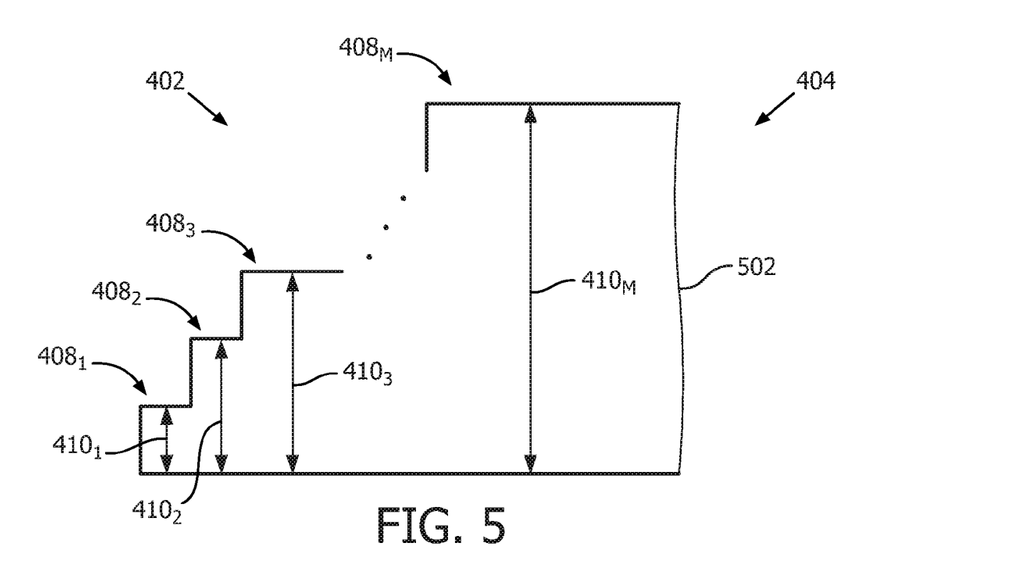
FIG. 5 schematically illustrates an example single component calibration phantom.

FIG. 5 illustrates a variation of FIG. 4 in which the calibration phantom 402 is a single structure 502 rather than a plurality of individual sheets 402 (as shown in FIG. 4) affixed to each other. Another variation includes a combination of FIGS. 4 and 5 in which individual element with multiple steps are affixed together. It is to be understood that the relative thickness of the material at each step and the offset of each step in FIGS. 4 and 5 are provided for explanatory purposes and are not limiting.

Returning to FIG. 2, at 200, the calibration phantom 402 is positioned in the examination region 106, via the subject support 108 and/or otherwise, so that a step 408 can be scanned.

At 202, a step of the calibration phantom 402 is scanned via an axial scan.

At 204, a count rate for each detector pixel and for each energy bin is determined from the thickness of the step and stored in a memory device.

At 206, it is determined whether another region, having a different thickness with respect to the first region, of the calibration phantom is to be scanned.

If it is determined that another step of the calibration phantom, having the different thickness, is to be scanned, then at 208, the calibration phantom is positioned in the examination region 106, via the subject support 108 and/or otherwise, to the next step 408 to be scanned, and acts 202-206 are repeated.

The number of scan may be based on the number of steps (which could be two to ten, twenty, fifty or more, for example). For example, each step can be scanned, or a sub-set of the steps can be scanned.

If it is determined that another step is not to be scanned, then at 210 an estimated count rate for each detector pixel, for each energy bin and for each scanned thickness is determined based on an analytical model. These estimates can be determined before, at the same time, and/or after the acts 202-208.

The estimates can be calculated using a C++ and/or other library, which provides an attenuation model, including angle dependent x-ray spectrum, attenuation properties of various materials, and the properties of photon counting detectors represented by a response function. A MATLAB® or other interface can be used.

At 212, the calibration factors 140 are generated based on the measured and the estimated values. For example, in one non-limiting instance the calibration factors 140 are generated as quotients of the estimates divided by the measurements. Generally, each correction factor is a value that maps or scales the measured value to the estimated value for a particular combination of pixel, bin and thickness.

By way of non-limiting example, where the measurement of the count rate is $M_{m,p,s}$ for all pixels p=1, . . . , $N_p$, energy bins b=1, . . . , $N_b$ and step sizes s=1, . . . , $N_S$ for a set x-ray flux and x-ray spectrum (e.g., determined by the tube anode current I and acceleration voltage U, bow-tie filter) as to be realized later in the actual scan protocol, the calculation of the calibration factors can be expressed as $C_{b,p,s}=V_{b,p,s}/M_{b,p,s}$, wherein $V_{b,p,s}$ is expected count rate calculated using the analytical model for the same x-ray flux and x-ray spectrum.

At 214, the calibration factors 140 are stored as a look up table (LUT) and/or otherwise in the memory device Turning to FIG. 3, an example method for calibrating the photon-counting detector with the calibration factors generated in FIG. 2 is illustrated.

At 302, a subject or object is scanned with the spectral scanner 100 and/or other spectral scanner having photon-counting detector pixels.

At 304, the signals, which are indicative of energies of detected photons, output by the photon-counting detector pixels are energy-resolved, as described herein and/or otherwise.

At 306, a calibration value for a detector pixel and a bin is generated by interpolation of at least two stored calibration factors for the same detector pixel and same bin, with one corresponding to a smaller thickness and the one corresponding to larger thickness, for the detector pixel/bin combination.

At 308, apply the calibration values respectively to the measurements of the corresponding detector pixel/bin combinations. Generally, each correction factor value converts a measured value to a set of corrected data that match to the analytical estimated values, for each pixel, bin, and thickness.

In one non-limiting instance, the calibration values are generated through interpolation of the calibration factors. By way of non-limiting example, this can be achieved by, for each measured x-ray intensity $m_{b,p}$, finding a step number $\hat{s}$, so that $M_{b,p,\hat{s}} \leq m_{b,p} < M_{b,p,\hat{s}+1}$, and calculating a corrected measurement $v_{b,p}=m_{b,p} \cdot \text{interp}(C_{b,p,\hat{s}}, C_{b,p,\hat{s}+1})$, where interp is a suitable interpolation function, such as a linear, polynomial, cubic spline, and/or other interpolation approach.

At 310, the corrected signals are decomposed and/or reconstructed.

Generally, the analytical model models the attenuation by the absorber, and the calibration scan characterizes the hardware specific deviations from the model.

The above acts may be implemented by way of computer readable instructions, encoded or embedded on computer readable storage medium (i.e., physical memory and other non-transitory medium), which, when executed by a microprocessor(s), cause the processor(s) to carry out the described acts. Additionally or alternatively, at least one of the computer readable instructions is carried by a signal, carrier wave and other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for determining calibration factors for calibrating photon-counting detectors of a spectral imaging system, comprising: combining, with a processor, a heuristic calibration of the photon-counting detectors and an analytical calibration of the photon-counting detectors, wherein the analytical calibration is based on an analytical model; and generating, with the processor, a set of photon-counting calibration factors based on the combining of the heuristic calibration and the analytical calibration applying, with the processor, the calibration factors to measured computed tomography (CT) energy-resolved data from the photon-counting detectors of the spectral imaging system, generating corrected data; decomposing, with the processor, the corrected data into energy dependent components using the analytical model; and performing a spectral CT scan of a subject or an object with the spectral imaging system, generating the measured CT energy-resolved data.

2. The method of claim 1, further comprising, for the heuristic calibration:
scanning a plurality of steps of a calibration phantom, wherein the calibration phantom is composed of a single material and each step has a known and different approximately uniform thickness, producing a signal indicative thereof; and
determining a measured count rate for each detector pixel, energy bin and step thickness combination from the signal.

3. The method of claim 2, further comprising, for the analytical calibration:
determining an estimated count rate for the combinations based on an analytical model of the analytical calibration.

4. The method of claim 3, further comprising:
decomposing the corrected signal into at least one of a Compton, a photo-electric, and one or more K-edge components.

5. The method of claim 4, determining the set of photon-counting calibration factors as quotients of the estimated count rates divided by the measured count rates.

6. The method of claim 2, wherein scanning at least includes:
positioning the calibration phantom in an examination region to scan a first step of the calibration phantom;
performing an axial scan of the first step of the calibration phantom;
positioning the calibration phantom in the examination region to scan a second step of the calibration phantom having a thickness that is different than the thickness of the first step of the calibration phantom; and
scanning the second step of the calibration phantom.

7. The method of claim 1, wherein scanning includes scanning the plurality of steps of the calibration phantom only once.

8. The method of claim 1, the applying, comprising:
scaling the measured energy-resolved data with the calibration factors to fit the analytical model.

9. The method of claim 1, the applying, comprising:
obtaining a first calibration factor for a detector pixel for a bin and a first thickness;
obtaining a second calibration factor for the detector pixel for the bin and a second thickness, wherein a thickness of interest lies between the first and second thickness;
generating a calibration value for the detector pixel and the bin by interpolation of the first and second calibration factors; and
calculating a product of a measured data for the detector pixel and the bin and the calibration value to generate the corrected data.

10. The method of claim 1, further comprising:
spectrally decomposing the corrected data into two or more energy dependent components.

11. The method of claim 10, further comprising:
reconstructing volumetric image data for at least one of the two or more energy dependent components.

12. A method for calibrating photon-counting detector pixels of a spectral imaging system, comprising:

applying a set of calibration factors to each measured value of each detector pixel/energy bin pair, wherein the calibration factors are determined based on a combination of a heuristic calibration of the photon-counting detector and an analytical calibration of the photon-counting detector, wherein the analytical calibration is based on an analytical model; and spectrally decomposing the calibrated data into two or more energy dependent components using the analytical model, wherein the calibration factors mitigate spectral distortion caused by a radiation intensity profile shaper that filters a radiation beam of a spectral CT scan performed by the spectral imaging system.

13. The method of claim 12, the applying, further comprising:

obtaining a first calibration factor for a detector pixel for a bin and a first thickness;

obtaining a second calibration factor for the detector pixel for the bin and a second thickness, wherein a thickness of interest lies between the first and second thickness;

generating a calibration value for the detector pixel and the bin by interpolation of the first and second calibration factors; and calculating a product of a measured data for the detector pixel and the bin and the calibration value, thereby generating calibrated data.

14. The method of claim 13, the calculating, comprising:
scaling the measured energy-resolved data with the calibration value to fit the analytical model.

15. The method of claim 13, further comprising:
spectrally decomposing the calibrated data into two or more energy dependent components.

16. The method of claim 15, further comprising:
reconstructing volumetric image data for at least one of the two or more energy dependent components.

17. The method of claim 12, further comprising:
combining a heuristic calibration of the photon-counting detectors and an analytical calibration of the photon-counting detectors; and generating the set of calibration factors based on the combining of the a heuristic calibration and the analytical calibration.

18. The method of claim 17, further comprising:
scanning a plurality of steps of a calibration phantom, wherein the calibration phantom is composed of a single material and each step has a known and different approximately uniform thickness, producing a signal indicative thereof;

determining a measured count rate for each detector pixel, energy bin and step thickness combination from the signal;

determining an estimated count rate for the combinations based on an analytical model of the analytical calibration; and determining the set of photon-counting calibration factors based on the measured count rates and the estimated count rates.

19. The method of claim 18, wherein scanning at least includes:

positioning the calibration phantom in an examination region to scan a first step of the calibration phantom;

performing an axial scan of the first step of the calibration phantom;

positioning the calibration phantom in the examination region to scan a second step of the calibration phantom having a thickness that is different than the thickness of the first step of the calibration phantom; and scanning the second step of the calibration phantom.

20. The method of claim 18, determining the set of photon-counting calibration factors as quotients of the estimated count rates divided by the measured count rates.

21. A system, comprising:

a calibration factor generator that determines a set of photon-counting calibration factors for photon-counting detector pixels of a spectral CT imaging system, wherein the calibration factor generator determines the set of photon-counting calibration factors based on counts for each detector pixel, energy bin, and thicknesses combination from data from a single scan, by the spectral CT imaging system, of a plurality of steps of a single phantom composed of a single material, where each step has a known and different approximately uniform thickness, and an analytical model that estimates counts for the same detector pixel, energy bin, and thicknesses combinations;

a data corrector that corrects measured data from the photon-counting detector pixels of subject or object produced in response to a scan of the subject or object with the spectral CT imaging system based on the set of photon-counting calibration factors, a signal decomposer that spectrally decomposes the corrected measured data into two or more energy dependent components using the same analytical model.

* * * * *